(12) United States Patent
Bürke et al.

(10) Patent No.: US 9,017,054 B2
(45) Date of Patent: Apr. 28, 2015

(54) PRESS MUFFLE

(75) Inventors: Harald Bürke, Frastanz (AT); Rudolf Jussel, Feldkirch-Gisingen (AT); Heinrich Kappert, Vaduz (LI); Gottfried Rohner, Altstätten (CH); Thomas Stampfer, Feldkirch-Tosters (AT)

(73) Assignee: Ivoclar Vivadent AG, Schaan (LI)

( * ) Notice: Subject to any disclaimer, the term of this patent is extended or adjusted under 35 U.S.C. 154(b) by 526 days.

(21) Appl. No.: 13/270,511

(22) Filed: Oct. 11, 2011

(65) Prior Publication Data

US 2012/0121752 A1 May 17, 2012

(30) Foreign Application Priority Data

Nov. 5, 2010 (EP) ..................... 10190129

(51) Int. Cl.
*B29C 43/56* (2006.01)
*A61C 13/20* (2006.01)

(52) U.S. Cl.
CPC ..................... *A61C 13/20* (2013.01)

(58) Field of Classification Search
USPC ............... 164/516–519, 361; 425/78, 470; 264/516–519, 361
See application file for complete search history.

(56) References Cited

U.S. PATENT DOCUMENTS 4,278,630 A * 7/1981 Scheicher ............... 264/122
2005/0211414 A1* 9/2005 Wiest et al. ............. 164/519

FOREIGN PATENT DOCUMENTS

| DE | 687 383 C | 1/1940 |
|----|-----------|--------|
| DE | 34 45 848 A1 | 6/1986 |
| DE | 38 44 151 A1 | 7/1990 |
| DE | 40 30 542 C1 | 3/1992 |
| GB | 461 104 A | 2/1937 |
| JP | 11 076270 A | 3/1999 |

* cited by examiner

Primary Examiner — Joseph S Del Sole
Assistant Examiner — Thukhanh T Nguyen
(74) Attorney, Agent, or Firm — Ann M. Knab; Thad McMurray

(57) ABSTRACT

The invention concerns a press muffle made of an embedding mass for the production of dental restoration parts, with the embedding mass comprising at least one weakly heat-conducting, in particular ceramic, basic powder, with up to 70%, in particular 2% to 40% of the entire embedding mass (12) consisting of an additive having a higher thermal conductivity than the basic powder.

19 Claims, 2 Drawing Sheets

PRESS MUFFLE

CROSS-REFERENCE TO RELATED APPLICATIONS

This application claims the benefit of European Patent Application No. 10 190 129.6 filed Nov. 5, 2010, which is hereby incorporated by reference in its entirety.

TECHNICAL FIELD

The invention concerns a press muffle made of an embedding mass.

BACKGROUND OF THE INVENTION

Press muffles for dental technology usually consist of ceramic embedding masses containing cristobalite, which are cast around a positive model of a dental restoration part. The dental restoration part or parts is/are preferably included in the muffle in a central position. The muffle is heated after having cured, such that the wax components completely disappear and shaping spaces for the dental restoration parts remain which can be filled with dental ceramics via a press channel.

For cost reasons, it is desirable to be able to press a number of dental restoration parts at a time, for which purpose the press channel is branched in a fashion similar to a tree and individual shaping spaces are connected with the press channel via connecting channels.

Due to the provision of multiple shaping spaces, the distance between the outer circumference and the respective shaping space differs. To maintain the quality of the dental restoration part, however, it is critical that a precise temperature profile is observed during the pressing process.

When putting into practice embedding masses for enameling furnaces, i.e., not pressing furnaces, it has become known from DE 38 44 151 to provide the embedding mass with chrome particles or tungsten particles in order to avoid any heat accumulation. This happens in immediate proximity to the dental restoration parts, in such a fashion that the chrome particles are in contact with the prime components there. However, this may easily lead to oxidation and to a discoloration of the prime components, which is unacceptable especially when the dental restoration part is used in the frontal region.

In order to equalize a temperature profile inside the muffle, it has been suggested furthermore to use a metal ring extending at the outer circumference of the muffle. This is supposed to have a supportive effect at the same time and to prevent the muffle from chipping or spalling during the pressing process. On the other hand, metal typically has a comparatively large coefficient of thermal expansion, such that the desired supportive effect is not provided during pressing to the extent desired.

Although temperature equalization can also be achieved without any problem by a corresponding waiting time, such a cycle time can then easily mean 8 hours, i.e., one entire work day, in case of large muffles with multiple shaping spaces, such as, for instance, 10-member bridges, which is not desired either.

SUMMARY

In contrast to this, the invention is based on providing a press muffle made of an embedding mass for the production of dental restoration parts in which the press muffle is clearly improved regarding handling in practice and cycle time, without any impairments to quality resulting from this.

In accordance with the present invention, it is intended that the press muffle made of an embedding mass consisting to a large extent of a ceramic powder having a low degree of thermal conductivity, is provided with an additive having a higher degree of thermal conductivity than the ceramic powder. Even this basic measure leads to a clearly improved thermal conductivity within the embedding mass, such that temperature equalization is achieved more quickly. Still, surprisingly the favorable features of the embedding mass consisting of a ceramic powder can be retained, in particular also the comparatively short setting time until the embedding mass has cured.

When the additive, which can for example consist of SiC particles, is uniformly spread, thermal coupling is considerably improved, already seen from the outer circumference of the muffle, since the absorption coefficient of the additive is higher than that of the basic powder. Surprisingly, however, a considerably improved temperature equalization is possible if the additive extends in a cloud-like fashion around the shaping spaces. Already in the pre-heating furnace, the temperature is set in a comparatively distinctly quicker fashion, and temperature equalization is achieved considerably faster than in the press muffles known so far.

In an advantageous embodiment, it is intended to provide the additive also at the outer circumference of the press muffle and colored, i.e., in a color which is different from white. This makes it possible to clearly improve absorption, above all when using conventional furnaces comprising tube heaters, for the heat absorption is considerably better.

In accordance with the present invention, it is particularly favorable in any case if the additive having the higher thermal conductivity completely surrounds the shaping spaces for the dental restoration parts. This can be achieved, for instance, by uniformly distributing the additive in the form of another powder within the embedding mass. Alternatively, it can also be intended that the further powder or the other particles extends like a sort of cage, a sort of coating or a cloud around the shaping spaces and provides temperature equalization. Surprisingly, this measure, in spite of the low degree of thermal conductivity of the ceramic powder of the embedding mass, leads to the presence of a strong temperature equalization in the central portion of the embedding mass which makes possible the desired temperature profile. Already the pre-heating process can be done more quickly, and also the firing of the dental restoration parts can be done in a fashion exactly matched with the desired temperature profile, even if the ceramic powder of the embedding mass has a basically known, rather low degree of thermal conductivity.

Surprisingly, the thermal coupling of the muffle is considerably improved due to the additive. This holds true even if a high proportion of conventional embedding mass is used and the additive is only provided, for instance, surrounding the shaping space or at the outer circumference of the muffle.

In an advantageous embodiment it is intended that the thermal conductivity of the additive is distinctly different from the thermal conductivity of the ceramic basic powder. For example, the difference can amount to about the factor 10, such that the ceramic basic powder is to be regarded as a temperature insulator, and the additive as a temperature conductor.

It is also particularly favorable if the grain sizes of the particles of the ceramic powder on the one hand and of the additive on the other hand are adapted to the requirements. Basically it is no problem to select the grain size of the additive to be larger than the grain size of the ceramic powder, unless the coefficient of thermal expansion of the additive is distinctly larger than that of the ceramic powder. If this is the case, an equally large or a smaller grain size can also be selected for the additive.

It is particularly favorable if measures are taken to prevent the dental restoration parts from getting into contact with non-noble metal particles of the additive. This can happen, for instance, by virtually providing a protective layer of ceramic basic powder for that area which immediately surrounds the shaping spaces. The protective layer can be selected to be rather thin and prevents the non-noble metal particles of the additive, which oxidize at high temperatures, such as 1500 or 1600° C., and which change their color as a result of the oxidation, from discoloring the dental restoration part. Alternatively, it is also possible to use noble-metal particles for the additive, which may then reach as far as to the shaping space.

The further powder can for example be silicon carbide or silicon nitride or any other suitable material with a high degree of thermal conductivity. Silicon carbide, for instance, has a thermal conductivity of 30 to 200 W/mK and a coefficient of thermal expansion of 3.4 to 5.8 $10^{-6}$/K, considered at 1000° C. What is particularly favorable, when using silicon carbide as the additive, is the combination of the low degree of thermal expansion and the high degree of thermal conductivity. In addition, the melting point of 2300° C. is clearly higher than the temperature ranges occurring in practice when firing dental restoration parts.

Preferably, a quartz powder is used as the embedding mass, which powder mainly contains cristobalite and has a low degree of thermal conductivity of, for example, 2 W/mK. Even if only small amounts of, for instance 5% of SiC powder are admixed, this will lead to an improvement of the overall thermal conductivity of the press muffle by 40%, which makes possible a significant reduction in cycle time.

A particularly favorable structure of the press muffle in accordance with the present invention can also be achieved by means of a zone layout of the additive. For instance, surrounding the shaping space or spaces, a pure basic powder may be cast first, and, adjacently to this, in particular, in the foot area of the muffle, an embedding mass containing SiC. By constructing the SiC-containing zone to be disc shaped, a good introduction of heat to the inside can be realized.

It is furthermore particularly favorable if the outer circumference of the press muffle is formed immediately by a zone containing SiC, or if the additive is positioned predominantly at the outer circumference. This leads to a distinct increase in surface roughness, and the introduction of heat is surprisingly improved considerably. This effect can be achieved in the same fashion by adding small shaped particles or by an enrichment with SiC powder at the outer circumference of the press muffle.

In accordance with the present invention, it is particularly favorable in this context that the absorption coefficient of silicon carbide is comparatively high, i.e., it amounts to about $\epsilon=0.9$. This leads to a particularly good absorption of the amount of heat introduced.

It is to be understood that the zoning and also the overall introduction of the additive can be adapted to the requirements in wide areas. As a result of enriching the embedding mass with an additive to an amount of up to 5%, the setting time of the embedding mass is not changed at all or not considerably; this holds equally true for the particular geometrical truth of the embedding mass.

In a preferable embodiment, it is intended that up to 70%, in particular 2% to 40%, of the entire embedding mass consists of an additive having a higher thermal conductivity than the basic powder.

In a preferable embodiment, it is intended that the thermal conductivity of the additive is higher than the thermal conductivity of the basic powder by the factor 3 to 100, in particular 8 to 60 times higher, and especially preferably 10 to 40 times higher.

In a preferable embodiment, it is intended that the additive is made up of another powder which particularly consists of particles of a metal, in particular of a noble metal.

In a preferable embodiment, it is intended that the further powder consists of silicon carbide and/or silicon nitride.

In a preferable embodiment, it is intended that the additive, in particular the further powder, is distributed around the dental restoration part and adjacent to it.

In a preferable embodiment, it is intended that in the entire area surrounding the shaping spaces for the dental restoration parts, the distribution of the additive, in particular the concentration of further powder, is higher than in the remaining portion of the press muffle.

In a preferable embodiment, it is intended that the press muffle is basically of cylindrical shape and the surrounding area horizontally surrounding the shaping spaces has an increased share in the additive, and in that the surrounding area equalizes the temperature of the shaping space.

In a preferable embodiment, it is intended that the press muffle is basically of cylindrical shape and the surrounding area vertically surrounding the shaping spaces has an increased share in the additive, and in that the surrounding area equalizes the temperature of the shaping space.

In a preferable embodiment, it is intended that the further powder and the ceramic powder are mixed to be homogeneous.

In a preferable embodiment, it is intended that the additive is of a different color than the ceramic powder.

In a preferable embodiment, it is intended that the additive is of a color other than white.

In a preferable embodiment, it is intended that the additive is made up of small shaped particles, in particular in the shape of spheres and/or pins and/or rings.

In a preferable embodiment, it is intended that the shaping space for dental restoration parts immediately surrounding the press muffle consists exclusively of the basic powder without any additive, in particular of a layer which measures less than one tenth of the diameter of the press muffle.

In a preferable embodiment, it is intended that the additive is introduced at the outer circumference of the press muffle in a high concentration, and in particular has larger-diameter particles than the basic powder.

In a preferable embodiment, it is intended that the additive is provided according to the type of a cloud in a distribution of concentrations within the embedding mass which, seen around the circumference of the press muffle, is basically equal and is low adjacent to the shaping space for dental restoration parts, then is quickly increased and is decreased subsequently, with the maximum concentration being in particular within half the radius, seen from the shaping space.

BRIEF DESCRIPTION OF THE DRAWINGS

Embodiments of the present invention will be more fully understood and appreciated by the following Detailed Description in conjunction with the accompanying drawings, in which.

DETAILED DESCRIPTION

Figure 1:
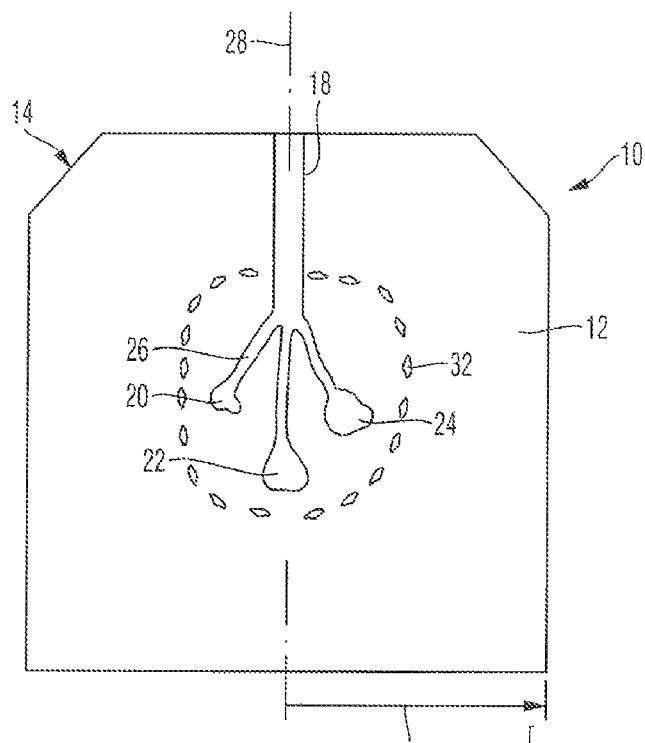
FIG. 1 a schematic view of a press muffle in one embodiment of the present invention.
Figure 2:
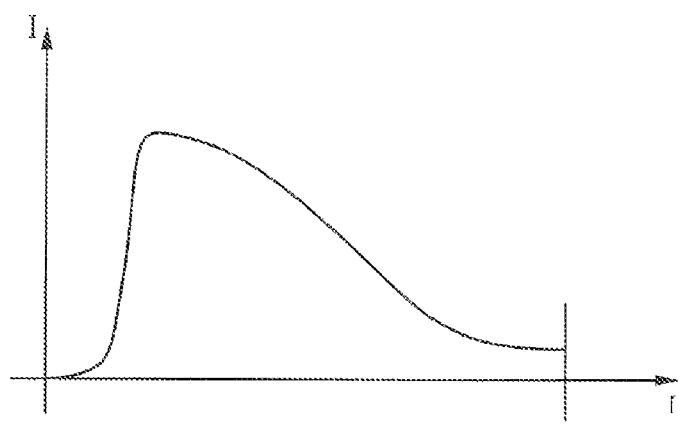
FIG. 2 the distribution of the additive seen in the radial direction over the press muffle in accordance with FIG. 1.

The press muffle 10 depicted in FIG. 1 consists of an embedding mass 12 which essentially extends in the shape of a cylinder after curing in a basically known fashion, the cylinder having a basically known taper 14 at the upper outer margin of press muffle 10.

By means of melting out respective wax bodies, a pressing channel 18 and shaping spaces 20, 22 and 24 are formed in press muffle 10, each of which is connected with the pressing channel 18 via connection channels 26.

Press muffle 10 extends basically in a circularly symmetric fashion around an axis 28 and has a radius 30 which is thus smaller than the height of the press muffle.

The embodiment of a press muffle 10 in accordance with the present invention depicted in FIG. 1 is provided with additive 32 in the form of particles, in accordance with the present invention, which particles are uniformly distributed around shaping spaces 20 to 24. The distribution is depicted here in a schematic fashion by means of particles 32, wherein it is to be understood that indeed there is only a corresponding zone of particles which causes an increased thermal conductivity for the press muffle in this position. This embodiment is particularly suited for equalizing the temperature between shaping spaces 20, 22 and 24. Also towards the outer radius, however, particles 32 are provided, in this embodiment, however, in lower quantity, such that also the increased thermal conductivity and the improved heat-absorption capacities of the particles 32 of the additive have a positive effect.

In this embodiment, the area immediately surrounding shaping spaces 20 to 24 is free of additive particles 32. This makes it possible to not only use silicon carbide particles, which are inert towards dental restoration ceramics, but also metal particles. Press furnaces are also used at low temperatures today, such as, for instance, at slightly more than 1000° C. or even at 900° C. This makes it possible to also use metal compounds and to guide the additive particles right to the shaping spaces.

Figure 3:
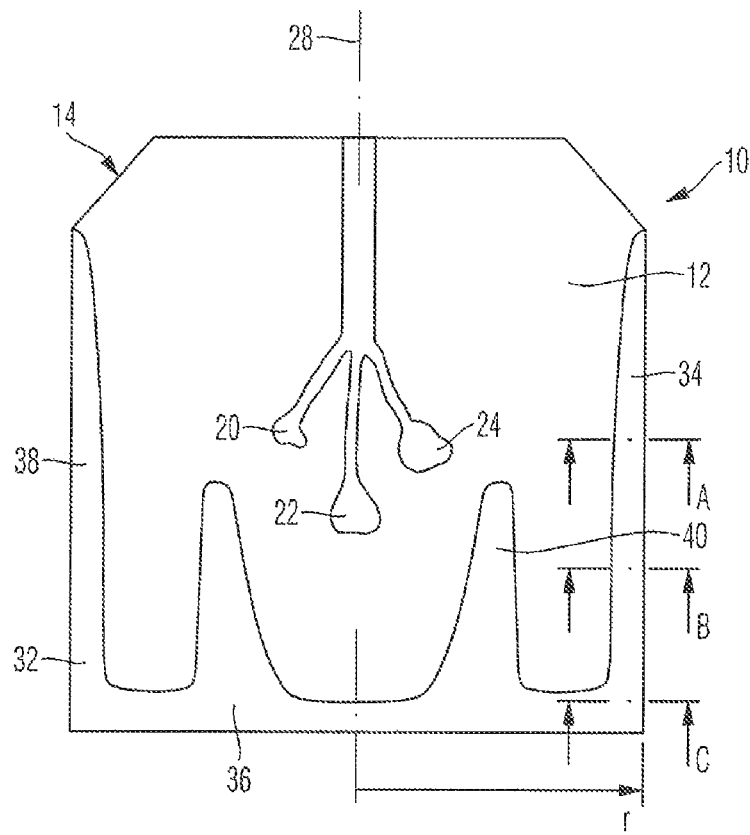
FIG. 3 a further embodiment of a press muffle in accordance with the present invention.

A modified embodiment of the press muffle in accordance with the present invention can be taken from FIG. 3. Equal reference numerals indicate equal components here. In this embodiment, a specially shaped zone 34 with particles 32 is provided. Zone 34 extends away over the bottom area 36 of press muffle 10, forming a sort of disc there. In addition, it extends over the entire outer wall 38 of the cylinder-shaped press muffle 10, forming a sort of hollow cylinder there. This combination results in an essentially pot-shaped layout of zone 34 with particles 32.

Moreover, in the embodiment in accordance with FIG. 3, a sort of interior pot 40 is provided, which is depicted in FIG. 3 in a basically schematic fashion, depicting areas of higher concentrations of particles 32 which extend into the area surrounding the hollow shaping spaces 20, 22 and 24. This guarantees a particularly good thermal coupling there, with the distance between the zone of interior pot 40 and shaping spaces 20, 22 and 24 being selected to be equal, such that the introduction of heat can be provided in a particularly well equalized fashion.

Figure 4:
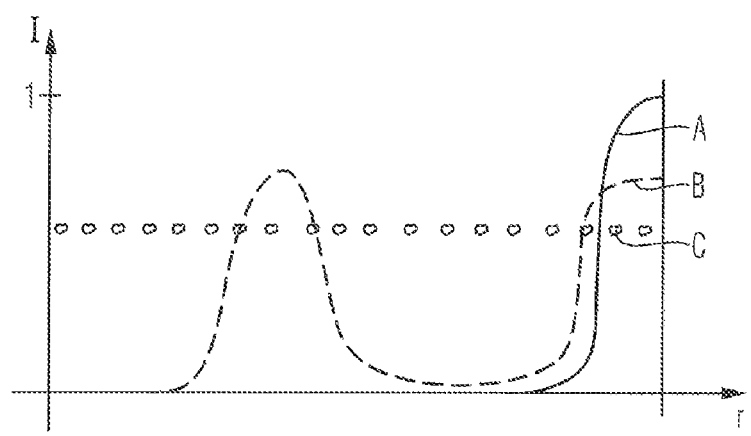
FIG. 4 a depiction of the concentration trace of the additive in the embodiment in accordance with FIG. 3.

The concentration trace of particles 32 in the different levels A, B, C, seen over radius R, is depicted in FIG. 4. It can be seen that at the outer circumference the overall concentration of particles 32 is particularly high, however, for maintaining geometrical truth, it is somewhat lower in the bottom area at C than at the level of the shaping spaces at A.

As can be seen, surrounding the shaping spaces, corresponding to curve A, the embedding mass is fabricated exclusively out of ceramic basic powder, i.e., free of any additive particles 32. Beneath the shaping spaces, corresponding to curve B, however, adjacently to shaping spaces 20 to 24, an area of higher concentration of particles 32 is provided, as is depicted corresponding to the broken curve B.

In the bottom area, i.e., in the area of disc 36, the concentration of particles is equal over the entire radial trace of press muffle 10.

It is to be understood that the embodiments of the invention depicted are to be seen merely as examples, and an adaptation to the respectively valid requirements and embedding masses can be made.

The invention claimed is:

1. Press muffle fabricated of an embedding mass for the production of dental restoration parts, the embedding mass comprising at least one weakly heat-conducting ceramic basic powder, wherein up to 70% of the entire embedding mass comprises an additive having a higher thermal conductivity than the basic powder, wherein the additive is distributed around the dental restoration part and adjacent to it, wherein the additive is provided according to a type of a cloud in a distribution of concentrations within the embedding mass (12) wherein it is disposed at around the circumference of the press muffle (10), in approximately equal thickness and is further disposed in a lower section of the press muffle adjacent to a shaping space for dental restoration parts, and is disposed at increased height from the lower section forming at least one peak, wherein the maximum concentration is within half a radius (30), as viewed from the shaping space.

2. Press muffle in accordance with claim 1, wherein 2% to 40% of the entire embedding mass (12) comprises an additive having a higher thermal conductivity than the basic powder.

3. Press muffle in accordance with claim 1, wherein the thermal conductivity of the additive is higher than the thermal conductivity of the basic powder by a factor of 3 to 120 times higher.

4. Press muffle in accordance with claim 3, wherein the thermal conductivity of the additive is higher than the thermal conductivity of the basic powder by a factor of 8 to 80 times higher.

5. Press muffle in accordance with claim 4, wherein the thermal conductivity of the additive is higher than the thermal conductivity of the basic powder by a factor of 10 to 40 times higher.

6. Press muffle in accordance with claim 1, wherein the additive is made up of a different powder than the ceramic basic powder, wherein the different powder comprises particles of a metal.

7. Press muffle in accordance with claim 1, wherein the additive is made up a different powder than the ceramic basic powder, wherein the different powder comprises particles of a noble metal.

8. Press muffle in accordance with claim 1, wherein the additive comprises silicon carbide and/or silicon nitride.

9. Press muffle in accordance with claim 1, wherein the press muffle (10) is basically of cylindrical shape and a surrounding area horizontally surrounding the shaping spaces (20, 22, 24) has an increased share in the additive, and wherein the surrounding area equalizes the temperature of the shaping space.

10. Press muffle in accordance with claim 1, wherein the press muffle (10) is basically of cylindrical shape and a surrounding area vertically surrounding the shaping spaces (20,

22, 24) has an increased share in the additive, and wherein the surrounding area equalizes the temperature of the shaping space.

11. Press muffle in accordance with claim 1, wherein the additive and the ceramic powder are mixed to be homogeneous.

12. Press muffle in accordance with claim 1, wherein the additive is of a different color than the ceramic powder.

13. Press muffle in accordance with claim 12, wherein the additive is of a color other than white.

14. Press muffle in accordance with claim 1, wherein the additive is made up of small shaped particles.

15. Press muffle in accordance with claim 1, wherein the small shaped particles comprise particles in the shape of spheres, pins, or rings or a mixture thereof.

16. Press muffle in accordance with claim 1, wherein a shaping space for dental restoration parts immediately surrounding the press muffle (10) consists exclusively of the basic powder without any additive.

17. Press muffle in accordance with claim 16, wherein the shaping space for dental restoration parts immediately surround the press muffle consists essentially of a layer which amounts to less than one tenth of the diameter of the press muffle (10).

18. Press muffle in accordance with claim 1, wherein the additive is introduced at the outer circumference of the press muffle (10) in a high concentration.

19. Press muffle in accordance with claim 18, wherein the additive has larger-diameter particles than the basic powder.

\* \* \* \* \*